US010058448B2

(12) United States Patent
Degroot et al.

(10) Patent No.: US 10,058,448 B2
(45) Date of Patent: Aug. 28, 2018

(54) ARM IMMERSION COOLING APPARATUS AND METHOD

(75) Inventors: David Degroot, Bel Air, MD (US);
Richard Gallimore, Milford, MA (US);
Gary Proulx, Harrisville, RI (US);
Karen Buehler, Northbridge, MA (US)

(73) Assignee: U.S. ARMY MEDICAL RESEARCH AND MATERIEL COMMAND, Washington, DC (US)

(*) Notice: Subject to any disclaimer, the term of this patent is extended or adjusted under 35 U.S.C. 154(b) by 1255 days.

(21) Appl. No.: 13/983,877

(22) PCT Filed: May 19, 2012

(86) PCT No.: PCT/US2012/038734
§ 371 (c)(1),
(2), (4) Date: Sep. 16, 2013

(87) PCT Pub. No.: WO2012/162199
PCT Pub. Date: Nov. 29, 2012

(65) Prior Publication Data
US 2014/0005761 A1  Jan. 2, 2014

Related U.S. Application Data (60) Provisional application No. 61/488,694, filed on May 20, 2011.

(51) Int. Cl.
| B60P 3/39 | (2006.01) |
| A61F 7/00 | (2006.01) |
| A61H 35/00 | (2006.01) |

(52) U.S. Cl.
CPC .............. *A61F 7/00* (2013.01); *A61H 35/00* (2013.01); *A61F 2007/0034* (2013.01);
(Continued)

(58) Field of Classification Search
CPC .............. A61H 33/00; A61H 2035/004; A61H 33/025; A61H 2203/02; A61H 33/0095;
(Continued)

(56) References Cited

U.S. PATENT DOCUMENTS

| 1,427,598 A | 8/1922 | Jackson |
| 1,812,971 A | 7/1931 | McCandles |

(Continued)

FOREIGN PATENT DOCUMENTS

| FR | 321700 A | 1/1903 |
| FR | 2598071 A1 | 11/1987 |
| GB | 119752 A | 10/1918 |

OTHER PUBLICATIONS

Honeywell, http://www.firerescue1.com/fire-products/fire-rehab/articles/409059-Rehab-chair-gets-to-the-core-of-heat-stress/, Kore Kooler, retrieved from the internet on Jul. 7, 2008.

(Continued)

*Primary Examiner* — Daniel Fowler
*Assistant Examiner* — Yasamin Ekrami
(74) *Attorney, Agent, or Firm* — Elizabeth Arwine; William Eshelman (57) ABSTRACT

A two person portable apparatus (10) for reducing the core temperature of one or more human beings includes a trough (14) made of a waterproof, flexible fabric (56) and a generally rectangular frame (12). Portions (68, 70, 72, 74) of the fabric (56) are looped over sides (24, 26, 28, 30) of the frame (12) so that the trough is supported by and suspended from the frame. The apparatus includes four legs (16, 18, 20, 22) hinged to corners of the frame and pivotable inwardly under the trough. Cooling water is placed in the trough and the hands and forearms of human beings are immersed in the cooling water.

17 Claims, 11 Drawing Sheets

(52) U.S. Cl.
CPC ............... *A61F 2007/0063* (2013.01); *A61H 2201/0107* (2013.01); *A61H 2201/0161* (2013.01); *A61H 2201/0214* (2013.01)

(58) Field of Classification Search
CPC .... A61H 2201/0142; A61H 2201/0214; A61F 7/00
See application file for complete search history.

(56) References Cited

U.S. PATENT DOCUMENTS

| | | | |
|---|---|---|---|
| 1,881,405 A | | 10/1932 | Haring |
| 2,581,883 A | * | 1/1952 | Rechler .................. A47K 3/164 |
| | | | 4/551 |
| 2,659,090 A | | 11/1953 | Westfahl |
| 3,232,502 A | * | 2/1966 | Kleinbortas ............ B60R 9/045 |
| | | | 224/314 |
| 3,799,228 A | * | 3/1974 | Crawford ................. A45F 4/00 |
| | | | 220/9.2 |
| 3,800,336 A | * | 4/1974 | Hoxeng .................. A47K 3/06 |
| | | | 4/587 |
| 4,277,855 A | * | 7/1981 | Poss ...................... A61H 33/06 |
| | | | 4/524 |
| 4,577,354 A | | 3/1986 | Stratton |
| 4,713,850 A | | 12/1987 | Flaherty et al. |
| 5,722,100 A | * | 3/1998 | Jozwiak ............... A47D 15/008 |
| | | | 4/572.1 |
| 6,421,853 B1 | | 7/2002 | Pecorelli et al. |
| 7,056,334 B2 | | 6/2006 | Lennox |
| 7,377,935 B2 | | 5/2008 | Schock et al. |
| 7,771,461 B2 | | 8/2010 | Schock et al. |
| 7,892,271 B2 | | 2/2011 | Schock et al. |
| 2004/0201262 A1 | | 10/2004 | McBride |
| 2005/0006931 A1 | * | 1/2005 | Meskill ................ A47B 3/0912 |
| | | | 297/158.4 |
| 2006/0069418 A1 | * | 3/2006 | Schock .................... A61F 7/00 |
| | | | 607/104 |
| 2007/0079436 A1 | * | 4/2007 | Na ..................... A61H 33/0095 |
| | | | 4/541.1 |
| 2008/0127897 A1 | * | 6/2008 | Flannery .............. A01K 1/0353 |
| | | | 119/28.5 |
| 2008/0221493 A1 | | 9/2008 | Schock et al. |
| 2008/0228245 A1 | | 9/2008 | Schock et al. |
| 2008/0306577 A1 | | 12/2008 | Schock et al. |
| 2011/0208275 A1 | | 8/2011 | Schock et al. |
| 2011/0238143 A1 | | 9/2011 | Schock et al. |

OTHER PUBLICATIONS

Malcolm Ross O'Neill : "Soldiers as the decisive edge", Winter Symposium and Exposition, Feb. 23, 2011 (Feb. 23, 2011). pp. 1-16, XP002682342, Retrieved from the Internet: URL:http:jjwww.crprogroup.comjeventnotebook/2011%20Winter%20WednesdayjDr%200Neill%20Wed%200815-0900.pdf [retrieved on Aug. 24, 2012] p. 11.

R. O'Hara et al., "Current and Future Cooling Technologies Using in Preventing Heat Illness and Improving Work Capacity for Battlefield Sodliers: Review of the Literature, "Military Medicine, vol. 173, No. 7, pp. 653-657, Jul. 2008.

* cited by examiner

ARM IMMERSION COOLING APPARATUS AND METHOD

CROSS-REFERENCE TO RELATED APPLICATIONS

The present application claims the benefit of priority of U.S. provisional patent application Ser. No. 61/488,694 filed on May 20, 2011, which is incorporated by reference herein.

STATEMENT OF GOVERNMENT INTEREST

The invention described herein may be manufactured, used and licensed by or for the United States Government.

BACKGROUND OF THE INVENTION

The invention relates in general to reducing the core temperature of human beings and in particular to lightweight, portable, non-powered apparatus and methods for reducing the core temperature of human beings.

Humans engage in physical activities including, for example, workplace operations, exercises, athletic competition and training, emergency rescue operations, and military combat and training. Risks associated with physical activities, particularly physical activities in a hot environment, are heat illness and heat stroke. Exertional heat stroke (EHS) may result when a human engages in strenuous physical activity for a prolonged period of time in a hot environment or when metabolic heat production is sufficiently elevated above resting.

Lowering the human body's elevated core temperature can reduce the risk of EHS. Various methods are known for lowering the body's core temperature. Cooling suits of various types are known. Cooling suits often interfere with the wearer's activity, add additional work burden to the wearer, and are expensive. Cooling suits are practical for some specialized activities, but are not a broadly applicable way of lowering body core temperature in physically active individuals. For large numbers of individuals, for example, soldiers in a training environment or team athletes, methods of avoiding heat stress have included ingesting substantial amounts of water, frequent rest periods, moving the individuals to a shady area, loosening or removing clothing, spraying the individuals with water misters, changing the time of day of training, and changing the order of training events. Nevertheless, decreased performance due to heat stress continues. As stated by R. O'Hara et al. (*Current and Future Cooling Technologies Used in Preventing Heat Illness and Improving Work Capacity for Battlefield Soldiers: Review of the Literature, Military Medicine*, Volume 173, Number 7, pp. 653-657, July 2008): "Currently, practical cooling devices that provide sustained cooling effects for battlefield soldiers are not available." (p. 653); and: "Clearly, there is a need for effective portable methods of cooling." (p. 655).

SUMMARY OF THE INVENTION

One aspect of the invention is an apparatus for reducing the core temperature of one or more human beings. One embodiment of the apparatus includes a fabric piece of waterproof, flexible material having a generally rectangular-shaped major portion with opposing long sides and opposing short sides and four flaps. Each flap extends from a respective one of the opposing long sides and the opposing short sides. The embodiment includes a generally rectangular frame with two short sides and two long sides. Each of the four flaps of the fabric piece is looped over a respective one of the short and long sides of the frame and attached to the major portion of the fabric piece. The major portion of the fabric piece forms sides and a bottom of a collapsible trough supported by and suspended from the frame.

Four legs have first ends disposed generally at four respective corners of the frame. Each leg is hinged at its first end to the frame and pivotable inwardly from an unfolded position of the apparatus, generally perpendicular to a plane of the frame, to a folded position of the apparatus, substantially parallel to the plane of the frame and under the trough. A pair of the legs disposed at one end of the long sides of the frame comprises a first leg section and a pair of the legs disposed at another end of the long sides of the frame comprises a second leg section.

The embodiment includes four longitudinal braces. Two of the braces are pivotally attached at first ends to a respective leg of the first leg section and two of the braces are pivotally attached at first ends to a respective bushing and a respective leg of the second leg section. In the unfolded position of the apparatus, each of the four braces is releaseably fixed to the rectangular frame at second ends of each of the four braces.

A weight of the embodiment is in a range of 45 pounds to 102 pounds. In an unfolded position of the apparatus, the collapsible trough has a fluid capacity in a range of 20 to 48 gallons.

A distance between the pair of legs in the second leg section is less than a distance between the pair of legs in the first leg section such that the first and second leg sections do not interfere in the folded position of the apparatus.

Cross-beams are disposed between the pairs of legs in each leg section. The cross-beams are separate from and spaced apart from a respective short side of the frame. Four corner gussets are disposed in respective internal corners of the frame. In the unfolded position of the apparatus, the four braces are releaseably fixed to long sides of the frame.

Four leg section braces are fixed at one end to a respective leg and at another end to a respective adjacent cross-beam. The leg section braces are diagonally oriented with respect to the legs and cross-beams and disposed further from the frame than the cross-beams in the unfolded position of the apparatus. Leg section gussets are disposed at corner intersections of the cross-beams and the legs on a same side of the cross-beams as the leg section braces.

Another aspect of the invention is a method of reducing the core temperature of a plurality of human beings simultaneously. One embodiment of the method includes providing an embodiment of the apparatus of the invention and placing cooling water in the trough of the embodiment. The hands and forearms of a plurality of human beings are simultaneously immersed in the trough.

An additional aspect of the invention is a method of making an apparatus for reducing the core temperature of one or more human beings. One embodiment of the method includes providing a fabric piece of waterproof, flexible material having a generally rectangular-shaped major portion with opposing long sides and opposing short sides and four flaps. Each flap extends from a respective one of the opposing long sides and the opposing short sides.

The embodiment includes providing a generally rectangular frame with two short sides and two long sides and looping each of the four flaps of the fabric piece over a respective one of the short and long sides of the frame. Then, each of the four flaps is attached to the major portion of the fabric piece.

The invention will be better understood, and further objects, features and advantages of the invention will become more apparent from the following description, taken in conjunction with the accompanying drawings.

BRIEF DESCRIPTION OF THE DRAWINGS

In the drawings, which are not necessarily to scale, like or corresponding parts are denoted by like or corresponding reference numerals.

DETAILED DESCRIPTION

An arm immersion cooling apparatus and method utilizes the greater heat transfer coefficient of water, compared to air, and the larger surface area-to-mass ratio of a human being's forearms compared to other body segments. The apparatus and method lower a human's core body temperature primarily by heat transfer through the hands and forearms. The hands and forearms are immersed in a cooling medium, such as water, contained in the apparatus. The apparatus is large enough for immersion of the hands and forearms of up to six adults. If needed, the apparatus can be used to immerse the complete torso of a single human to accelerate the cooling process. The large volume of cooling medium helps accelerate heat transfer from the users. The ease of use facilitates demand for and acceptance of the apparatus.

Importantly, the apparatus is inexpensive to manufacture and is portable by two people. Many features of the apparatus contribute to its two person portability. The weight of the apparatus (without water) is in a range of about of about 45 to about 102 pounds, preferably in the range of about 50 to about 70 pounds, most preferably about 60 pounds. In the transportation (folded) position, the most preferred size of the apparatus is about 62 inches long, 24 inches wide and about 4 inches deep. Of course, variations in the overall dimensions of the apparatus are possible. Exemplary variations are 56 to 68 inches long, 20 to 28 inches wide, and 2 to 8 inches deep. The inventive apparatus can accommodate up to six adults simultaneously for hand and forearm immersion or one adult for torso immersion. The apparatus is low maintenance, sized for ease of transport, easy to set up for use, and easy to take down for transportation.

FIGS. 1A-1D are front, top, left end, and right end views, respectively, of one embodiment of an apparatus 10 for cooling one or more human beings. Of course, embodiments of the invention that differ from apparatus 10 may be included in the literal or equivalent scope of the patent claims.

Apparatus 10 includes a generally rectangular frame 12 and four legs 16, 18, 20, 22. A collapsible trough 14 is supported by and suspended from frame 12. Legs 16-22 have respective first ends 16a, 18a, 20a, 22a disposed generally at four respective corners of frame 12. Legs 16-22 are hinged at first ends 16a-22a to frame 12. Hinges 13 are used to mount legs 16-22 to frame 12. From the unfolded position (shown in FIGS. 1A-D) where legs 16-22 are generally perpendicular to the plane of frame 12, legs 16-22 are inwardly pivotable to a folded position where legs 16-22 are substantially parallel to the plane of frame 12 and disposed under trough 14.

Figure 10A:
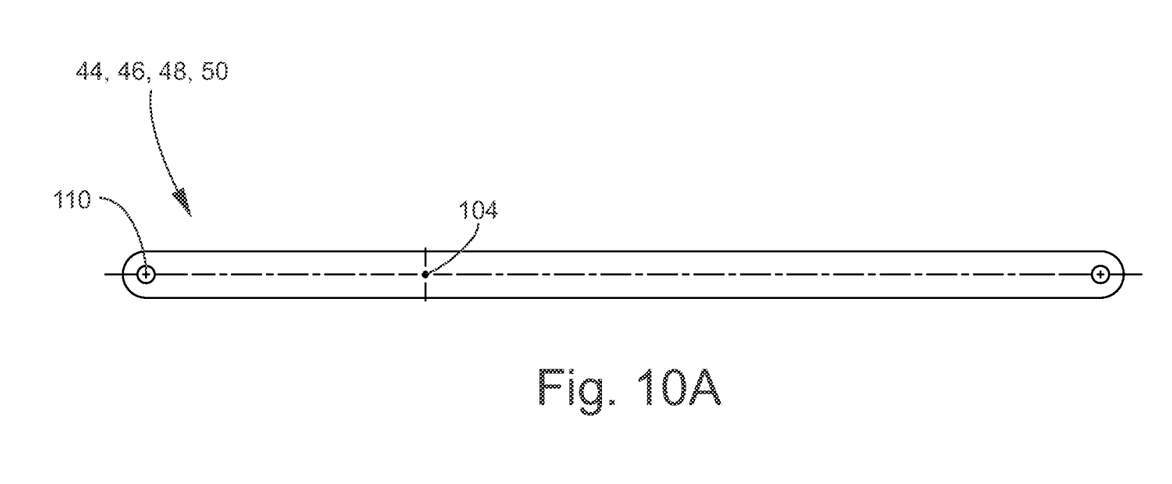
FIGS. 10A and 10B are front and end views, respectively, of a brace for the leg and frame.
Figure 10B:
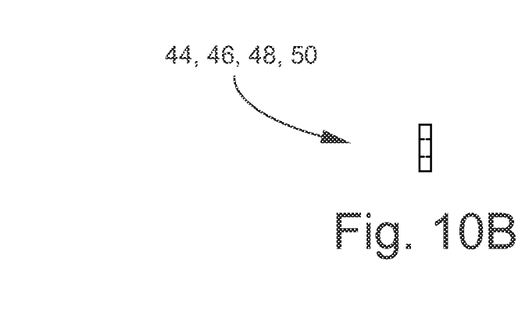

Apparatus 10 includes four longitudinal braces 44, 46, 48, 50. FIGS. 10A and 10B are detailed views of braces 44, 46, 48, 50. Two of the braces 44, 46 are pivotally attached at first ends 44a, 46a to respective legs 16, 18 and two of the braces 48, 50 are pivotally attached at first ends 48a, 50a to respective bushings 52, 54 (FIGS. 7A-B) and legs 20, 22. The first ends 44a-50a of braces 44-50 are attached using fasteners inserted in openings 96 (FIG. 6A) in legs 16-22.

In the unfolded position of apparatus 10 shown in FIGS. 1A-D, second ends 44b, 46b, 48b, 50b of each of the four braces 44-50 are releaseably fixed to rectangular frame 12. Quick-release pins 86 are used for releaseably fixing the four braces 44-50 to frame 12. Pins 86 pass through grommets 90 (FIG. 2) placed in openings 77 (FIG. 4) in flaps 70, 74 and through openings 29 (FIGS. 3A and 3C) in long sides 28, 30 of frame 12. A lanyard 88 is provided for each pin 86. One end of lanyard 88 is fixed to pin 86 and another end of lanyard 88 is fixed to a fastener in opening 104 (FIG. 10A) in braces 44-50. Cinching straps 106, for example, straps with hook and loop fasteners, are also fixed to a fastener in opening 104. Straps 106 are used to secure legs 16-22 in the folded position parallel to the plane of frame 12.

Figure 2:
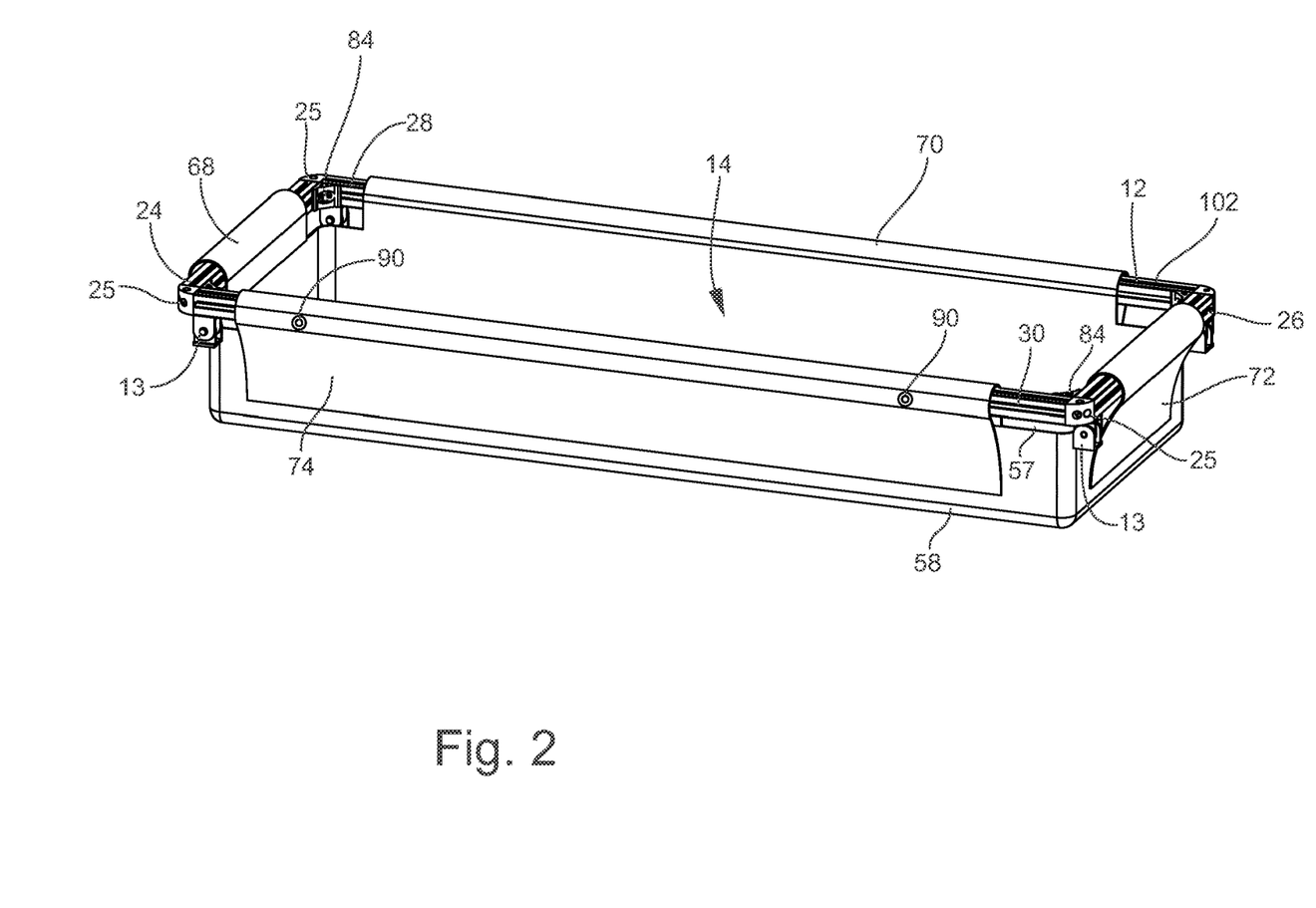
FIG. 2 is a perspective view of a portion of the apparatus of FIGS. 1A-1D.
Figures 3A, 3B, 3C:
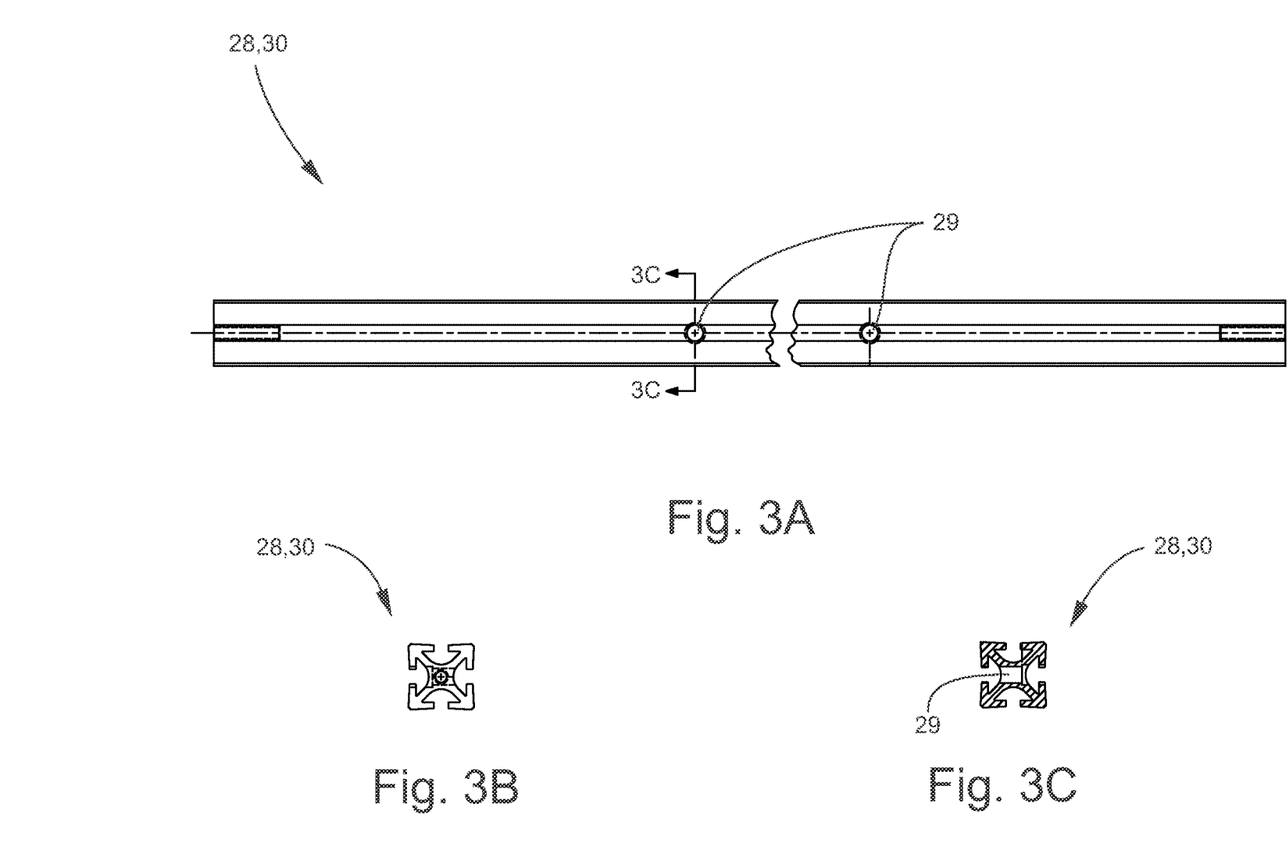
FIGS. 3A, 3B, and 3C are front, end, and sectional views, respectively, of a side of the frame of the apparatus of FIGS. 1A-D. The view in FIG. 3C is taken along the line 3C-3C of FIG. 3A.

FIG. 2 is a perspective view of frame 12 and trough 14 of apparatus 10. Frame 12 includes long sides 28, 30 and short sides 24, 26. Frame 12 is made of a lightweight metal, such as, for example, aluminum or aluminum alloy. Frame 12 may also be made of non-metallic materials, such as plastics, for example. Sides 24, 26, 28, 30 may have various shapes or cross-sections. Adequate strength and low weight are important factors for all components of apparatus 10, including frame 12. In one embodiment, frame 12 is made of aluminum and sides 24-30 have a cross-section shown in the end view of sides 28, 30 in FIG. 3B. Ends of sides 24-30 are joined by, for example, castle corners 25. Corner gussets 84 are fixed in each of the four internal corners of frame 12. Hinges 13 are mounted on short side 26 at one end of frame 12 and on long sides 28, 30 at the other end of frame 12. Components of frame 12 are available from, for example, Frame-World, Inc., 9116 Virginia Road, Lake in the Hills, Ill. 60156 USA.

Figure 1A:
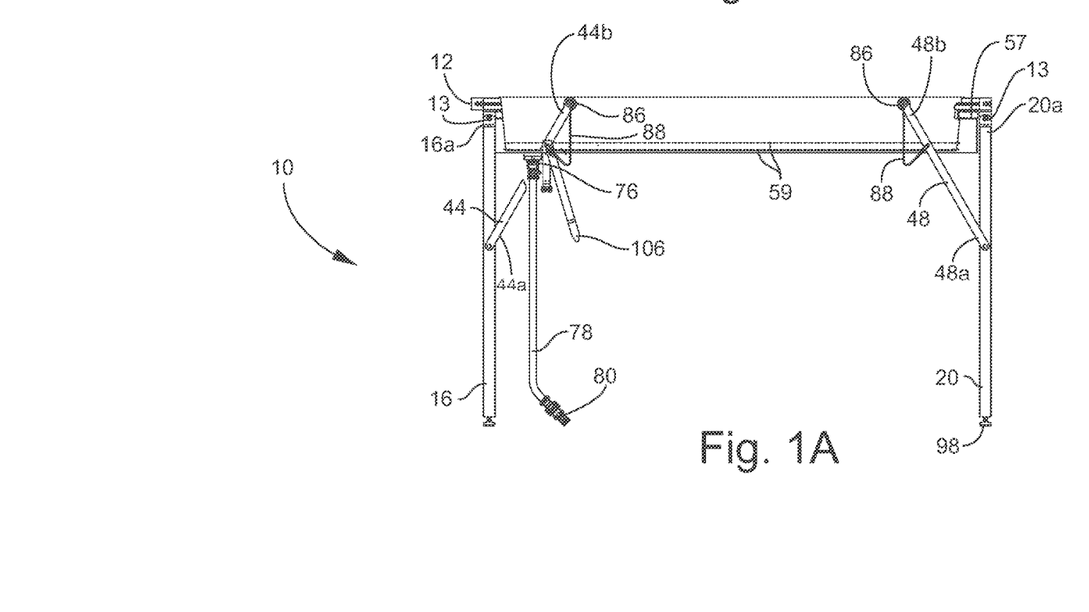
FIGS. 1A-1D are front, top, left end, and right end views, respectively, of one embodiment of an apparatus for cooling one or more human beings.
Figure 1B:
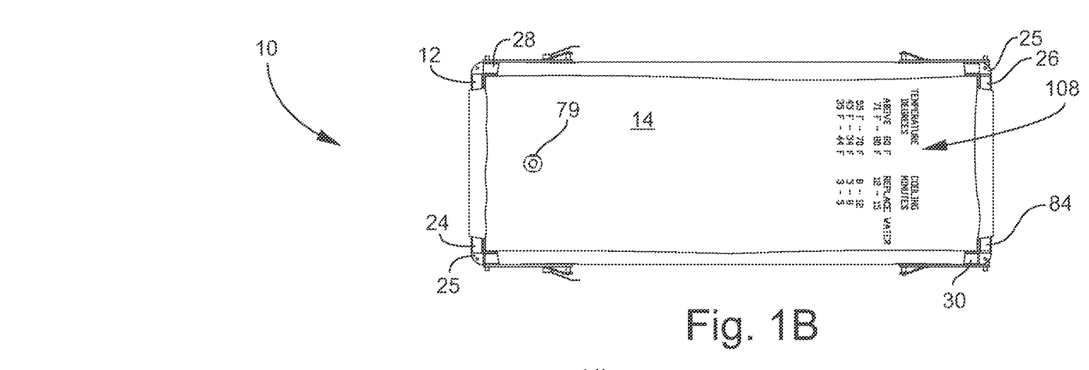
Figure 1C:
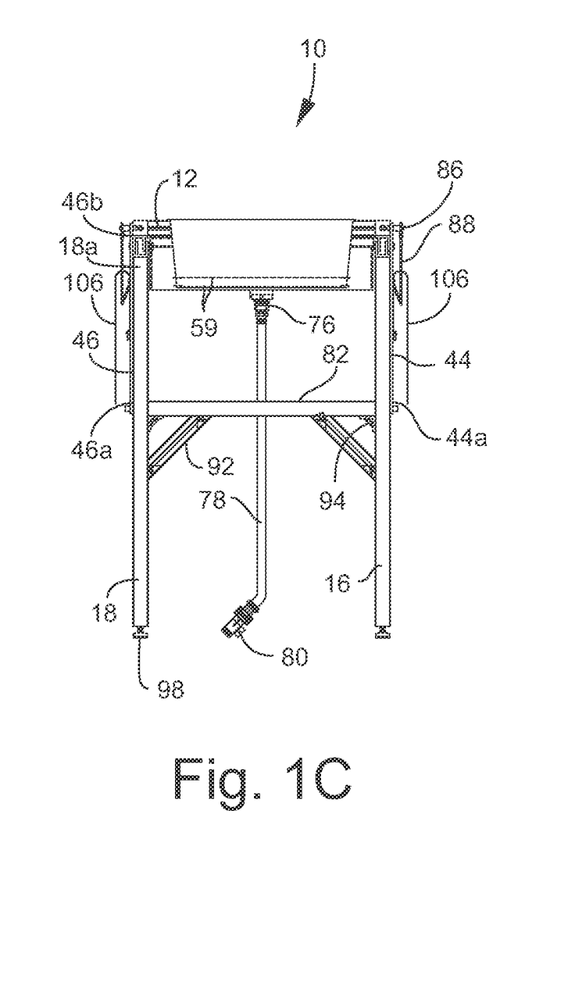
Figure 1D:
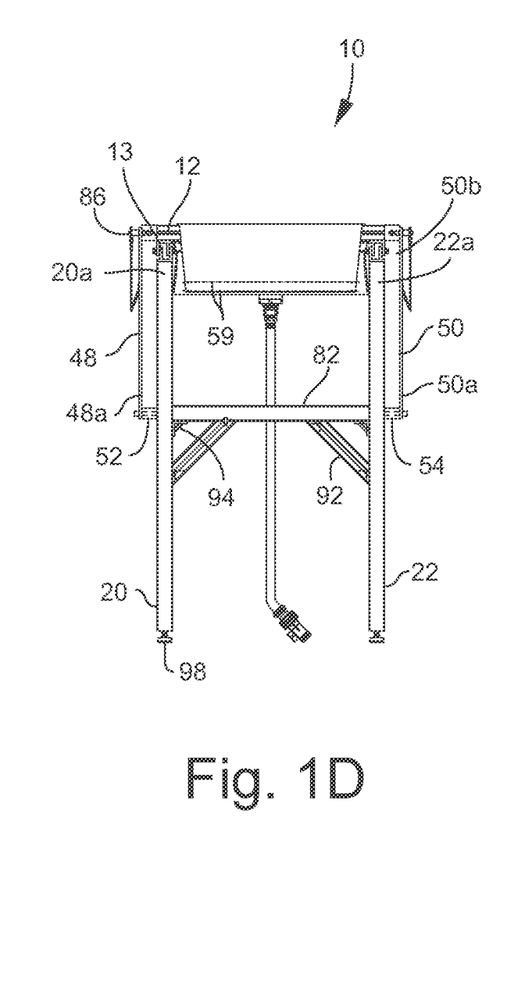
Figure 4:
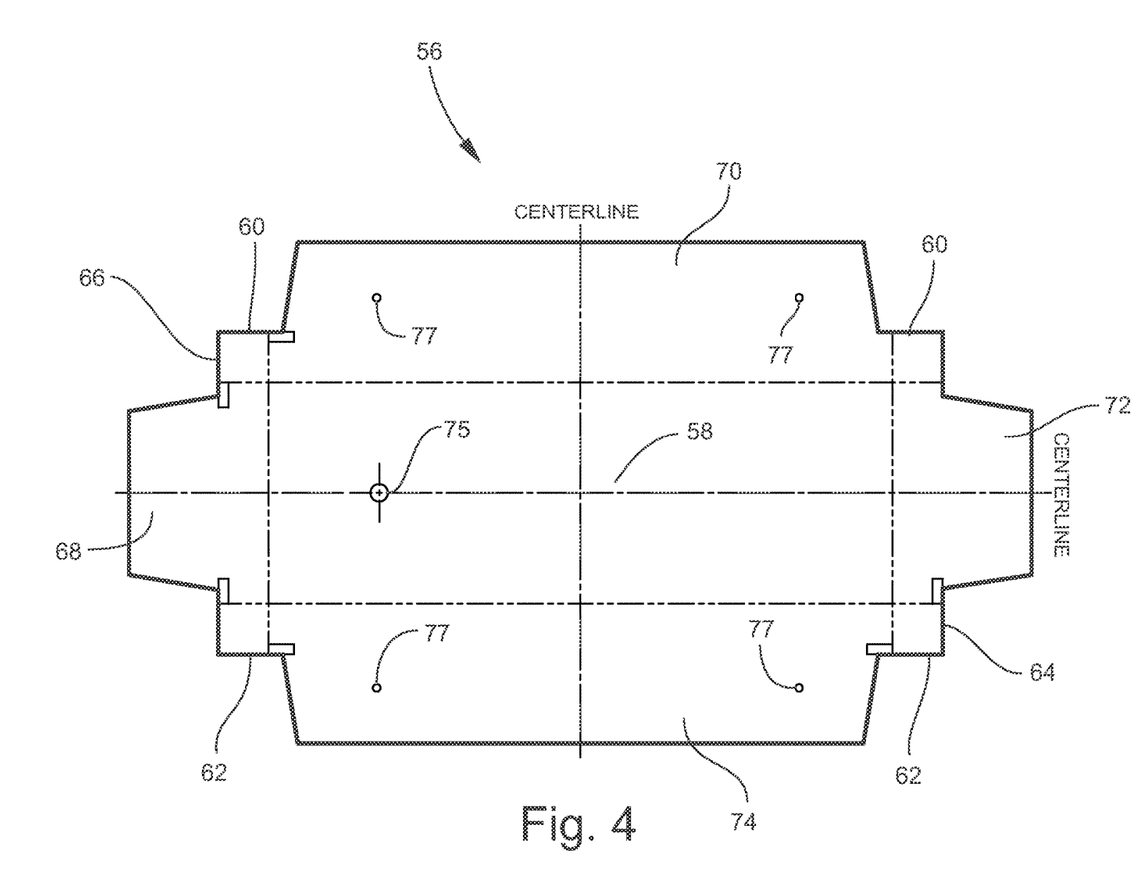
FIG. 4 is a top view of a fabric piece for constructing a trough for the apparatus of FIGS. 1A-D.

FIG. 4 is a plan view of a fabric piece 56 used to construct trough 14. Fabric piece 56 is a waterproof, flexible fabric (for example, tent fabric) having a generally rectangular-shaped major portion 58 with opposing long sides 60, 62 and opposing short sides 64, 66. Horizontal and vertical center lines of fabric piece 56 are shown by broken lines. Four exemplary fold lines of fabric piece 56 are also shown in broken lines. Four flaps 68, 70, 72, 74 extend from respective sides 66, 60, 64, 62. As shown in FIG. 2, each of the four flaps 68-70 of fabric piece 56 is looped over a respective one of the sides 26, 30, 24, 28 of frame 12 and attached to major portion 58 of fabric piece 56 using, for example, one or more rows of stitching 59 (FIGS. 1A, 1C, 1D). Major portion 58 of fabric piece 56 forms the sides and bottom of trough 14. Opening 75 (FIG. 4) in fabric piece 56 is fitted with a grommet 79 (FIG. 1B). A drain fitting 76 (FIG. 1A) is threaded in grommet 79. A drain hose 78 with a shut-off valve 79 is connected to drain fitting 76 for selectively draining water from trough 14. Webbing strips 57 (FIG. 2) are stitched around the upper portion of the corners of trough 14 for reinforcement.

For effective immersion of the hands and forearms, the depth of cooling medium, for example, water, in trough 14 should be at least about three inches. Preferably, the depth of water in trough 14 is from four to six inches and the volume of water is about 20 to 48 gallons, preferably about 37-40 gallons. A time/temperature table 108 (FIG. 1B) may be stenciled on the bottom of trough 14 for easy reference by users. A durable thermometer (not shown) may be fixed in trough 14 and used in conjunction with table 108.

Figure 9A:
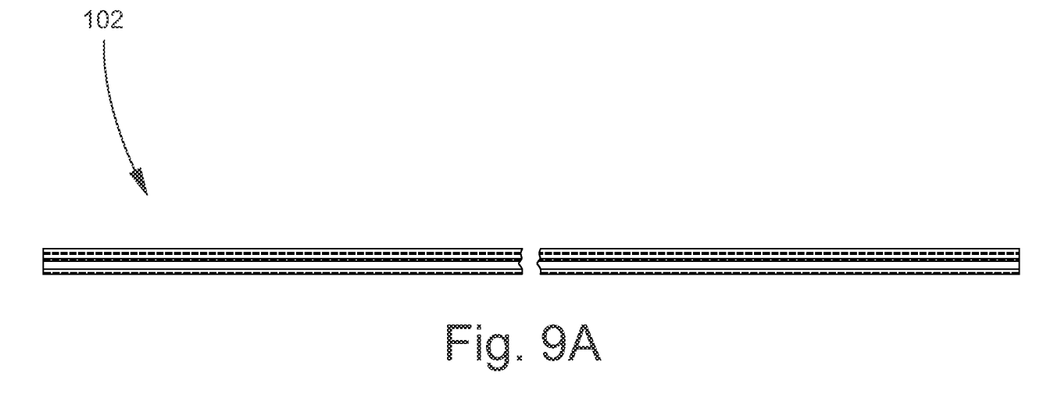
FIGS. 9A and 9B are front and end views, respectively, of a concave top frame insert.
Figure 9B:
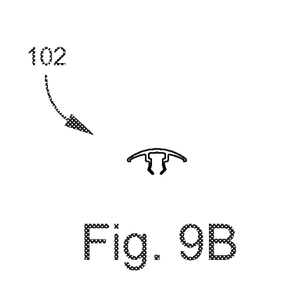

The top surfaces of the four sides 24-30 of frame 12 are preferably rounded to reduce wear on fabric piece 56. One way to round the top surfaces is to insert concave rail inserts 102 (FIGS. 9A and 9B) into the top surface of each side 24-30.

Figure 5A:
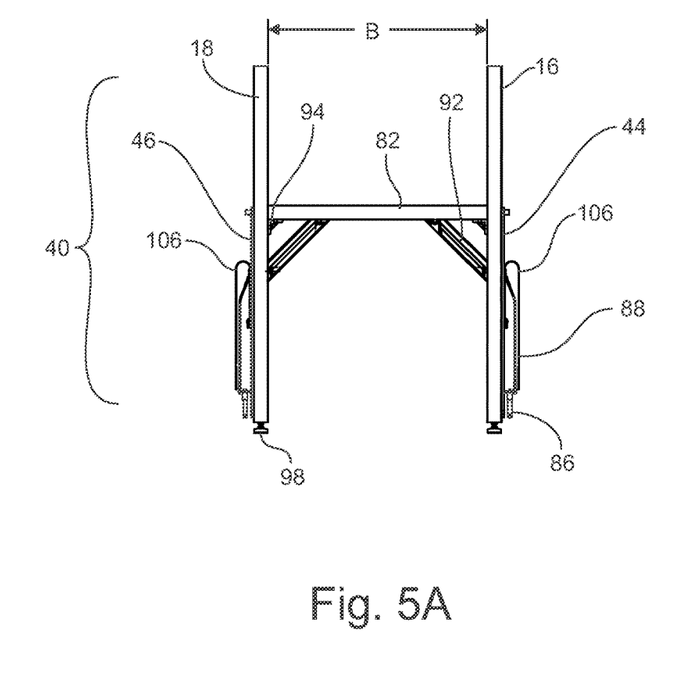
FIGS. 5A and 5B are end views of opposing leg sections of the apparatus of FIGS. 1A-1D (frame and trough are not shown).
Figure 5B:
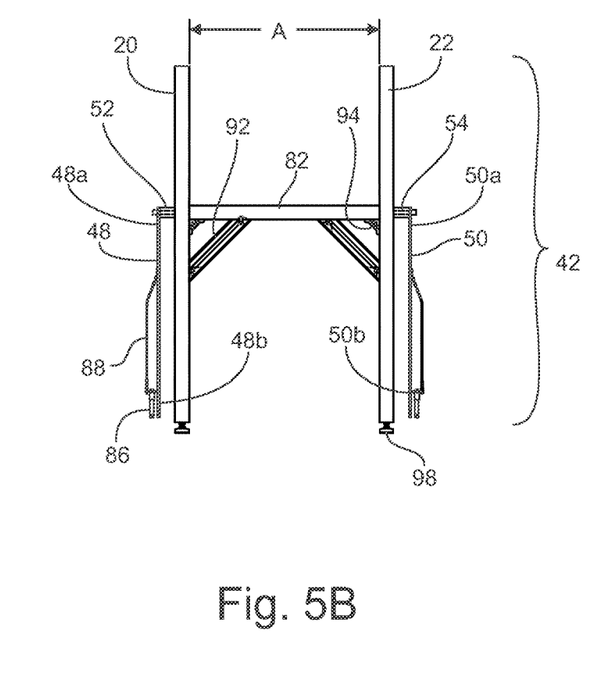

The pair of legs 16, 18 disposed at one end of long sides 28, 30 of frame 12 comprises a first leg section 40 (FIG. 5A) and the pair of legs 20, 22 disposed at another end of long sides 28, 30 of frame 12 comprises a second leg section 42 (FIG. 5B). The distance A between the pair of legs 20, 22 in second leg section 42 is less than the distance B between the pair of legs 16, 18 in the first leg section 40 such that the first and second leg sections 40, 42 do not interfere in the folded position of apparatus 10. That is, when leg sections 40, 42 are pivoted inwardly towards each other under the trough 14, legs 16, 18 are offset from legs 20, 22 so that both pairs of legs may be fully folded parallel to the plane of frame 14 without interference between the legs. The offset feature of the leg sections is important when the length of the legs is more than about one half the length of apparatus 10.

Figure 8A:
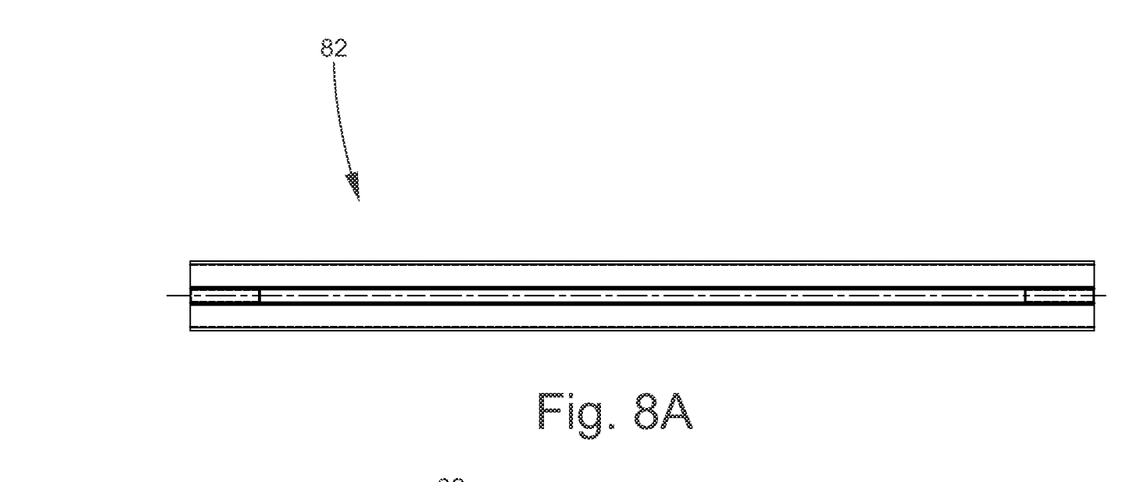
FIGS. 8A and 8B are front and end views, respectively, of a cross-beam.
Figure 8B:
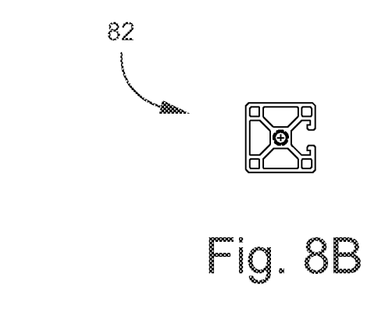

Each leg section 40, 42 includes a cross-beam 82 disposed between the pairs of legs in each leg section. Cross-beam 82 is shown in detail in FIGS. 8A and 8B. Cross-beams 82 are separate from and spaced apart from respective short sides 26, 24 (FIG. 2) of frame 12. Each leg section 40, 42 includes a pair of diagonal braces 92. Each brace 92 is fixed at one end to a respective leg 16-22 and at another end to a respective adjacent cross-beam 82. Braces 92 are diagonally oriented with respect to legs 16-22 and cross-beams 82 and disposed further from frame 12 than cross-beams 82. Gussets 94 are disposed at the intersection of cross-beams 82 and legs 16-22 on the same side of cross-beams 82 as diagonal braces 92.

Figure 6A:
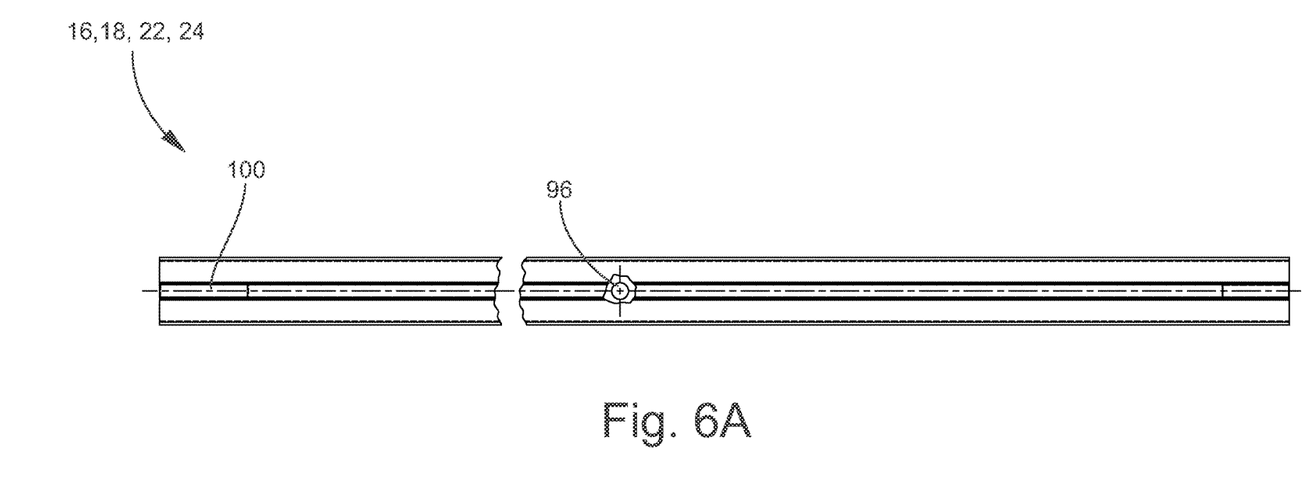
FIGS. 6A, 6B, and 6C are front, left end, and right end views, respectively, of a leg for the apparatus of FIGS. 1A-1D.
Figure 6B:
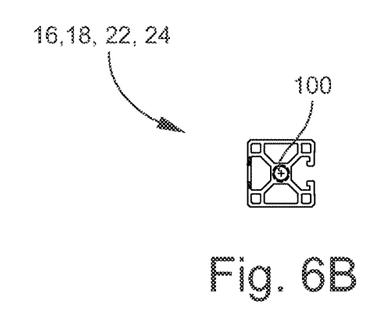
Figure 6C:
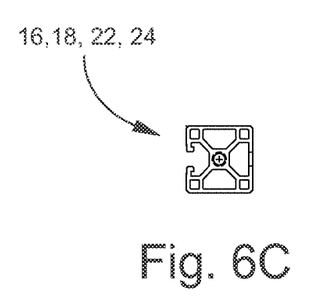
Figure 7A:
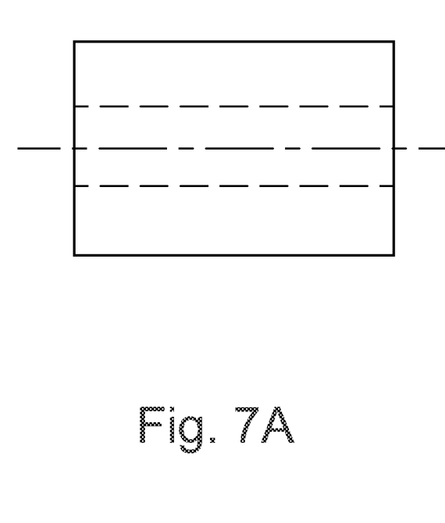
FIGS. 7A and 7B are front and end views, respectively, of a bushing.
Figure 7B:
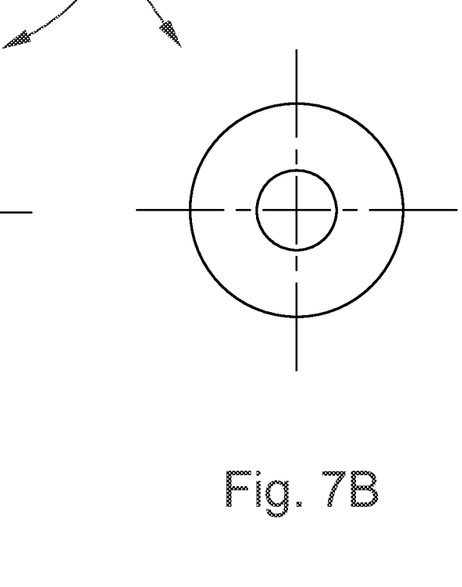

Legs 16-22 may have the shape or cross-section shown in FIGS. 6A-C. Adjusters 98 (FIGS. 5A-B) are provided on each leg to help level apparatus 10. Adjusters 98 thread into openings 100 (FIGS. 6A and 6B) in the bottom of each leg. Adjusters 98 are primarily for leveling apparatus 10 and not intended to vary the overall working height of apparatus 10. Legs with a large amount of length adjustment, such as telescoping legs, add undesirable cost and weight to the apparatus. In this regard, the length of legs 16-22 is generally fixed and represents a compromise to accommodate humans of greater or lesser than average stature. Legs 16-22 have a length in the range of about 30 to about 43 inches, and preferably about 35 to about 38 inches.

For transportation and storage, apparatus 10 is in a folded position (not shown) with leg sections 40, 42 pivoted under collapsed trough 14 and substantially parallel to the plane of frame 12. To use apparatus 10, cinching straps 106 are disengaged so that leg sections 40, 42 may be pivoted away from trough 14 and perpendicular to frame 12. The second ends 44b, 46b, 48b, 50b of each of the four braces 44, 46, 48, 50 are pivoted upward toward frame 12. Quick-release pins 86 are inserted through openings 110 (FIG. 10A) in second ends 44b-50b and through openings 29 (FIGS. 3A and 3C) in long sides 28, 30 of frame 12. Leg adjusters 98 are used to level apparatus 10. Cooling water is then placed in trough 14 to a depth of at least three inches and preferably more, up to six inches.

The cooling water temperature should be no more than 80 degrees F. Preferably, the cooling water is cooler than 80 degrees F. but no cooler than 35 degrees F. Up to six users may then simultaneously immerse their hands and forearms in trough 14. Depending on the temperature of the cooling water, the length of time of immersion may vary, for example, from three minutes to fifteen minutes, as shown by the time/temperature table 108 in FIG. 1B. Prior to or when the water in the trough has warmed to above 80 degrees F., some or all of the water can be drained out of the trough 14 through drain fitting 76 and hose 78 and cooler water can added to trough 14.

Because of the relatively short immersion time required, a single apparatus 10 may be sufficient for cooling a group of 16 to 44 individuals. A plurality of apparatus 10 may, of course, be used.

User acceptance of any new product, apparatus, or technique is highly unpredictable. Multiple apparatus 10 were distributed for testing to the U.S. Army Airborne School, Ranger Training Brigade, Ft. Benning, Ga. Initial results indicate positive user acceptance, reduction in heat injuries and heat stroke, and improved soldier performance. Additional apparatus 10 have been requested and mass production of apparatus 10 is planned. Non-military uses may include sports teams, athletic events, and civilian occupations in hot environments.

The details, materials, steps and arrangement of parts have been described and illustrated to explain the nature of the invention. It will be understood that many changes in the details, materials, steps and arrangement of parts may be made by those skilled in the art, within the principle and scope of the invention, as expressed in the appended claims and equivalents thereof.

What is claimed is:

1. An apparatus (10) for reducing the core temperature of one or more human beings, comprising:

a fabric piece (56) of waterproof, flexible material having a generally rectangular-shaped major portion (58) with opposing long sides (60, 62) and opposing short sides (64, 66) and four flaps (68, 70, 72, 74), each flap extending from a respective one of the opposing long sides and the opposing short sides;

a generally rectangular frame (12) with two short sides (24, 26) and two long sides (28, 30) wherein each long side is a member having no hinged or pivoted portion, each of the four flaps of the fabric piece being looped over a respective one of the short and long sides of the frame and attached to the major portion of the fabric piece, the major portion of the fabric piece forming sides and a bottom of a collapsible trough (14) supported by and suspended from the frame (12);

four legs (16, 18, 20, 22) having first ends (16a, 18a, 20a, 22a) disposed generally at four respective corners of the frame (12), each leg being hinged at its first end to the frame and pivotable inwardly from an unfolded position of the apparatus (10), generally perpendicular to a plane of the frame, to a folded position of the apparatus (10), substantially parallel to the plane of the frame and under the trough (14), wherein a pair of the legs (16, 18) disposed at one end of the long sides of the frame (12) comprises a first leg section (40) and a pair of the legs (20, 22) disposed at another end of the long sides of the frame (12) comprises a second leg section (42);

only two bushings (52, 54); and four longitudinal braces (44, 46, 48, 50), two of the braces (44, 46) being pivotally attached at first ends (44a, 46a) to a respective leg (16, 18) of the first leg section (40) and two of the braces (48, 50) being pivotally attached at first ends (48a, 50a) to a respective one of the only two bushings (52, 54) and a respective leg (20, 22) of the second leg section (42) and, in the unfolded position of the apparatus (10), each of the four braces (44, 46, 48, 50) being releaseably fixed to the rectangular frame (12) at second ends (44b, 46b, 48b, 50b) of each of the four braces (44, 46, 48, 50);

wherein a weight of the apparatus (10) is in a range of 45 pounds to 102 pounds and the fabric piece has a strength to support a weight of at least 20 gallons of water in the collapsible trough.

2. The apparatus of claim 1, wherein the frame (12) comprises aluminum.

3. The apparatus of claim 1, further comprising a drain fitting (76) inserted in the bottom of the trough (14).

4. The apparatus of claim 1, wherein, in an unfolded position of the apparatus, the collapsible trough (14) has a fluid capacity in a range of 20 to 48 gallons.

5. The apparatus of claim 3, further comprising a hose (78) attached to the drain fitting (76), the hose (78) including a shut-off valve (80).

6. The apparatus of claim 4, wherein a distance (A) between the pair of legs (20, 22) in the second leg section (42) is less than a distance (B) between the pair of legs (16, 18) in the first leg section (40) such that the first and second leg sections (40, 42) do not interfere in the folded position of the apparatus (10).

7. The apparatus of claim 6, further comprising a cross-beam (82) disposed between the pairs of legs in each leg section (42, 44), the cross-beam (82) being separate from and spaced apart from a respective short side (26, 24) of the frame (12).

8. The apparatus of claim 7, further comprising four corner gussets (84) disposed in respective internal corners of the frame (12).

9. The apparatus of claim 8, wherein, in the unfolded position of the apparatus (10), the four braces (44, 46, 48, 50) are releaseably fixed to long sides (28, 30) of the frame (12).

10. The apparatus of claim 9, further comprising quick-release pins (86) for releaseably fixing the four braces (44, 46, 48, 50) to the frame (12).

11. The apparatus of claim 10, wherein the quick-release pins (86) pass through the four flaps (68, 70, 72, 74).

12. The apparatus of claim 9, further comprising four leg section braces (92), each leg section brace (92) being fixed at one end to a respective leg (16, 18, 20, 22) and at another end to a respective adjacent cross-beam (82), the leg section braces (92) being diagonally oriented with respect to the legs (16, 18, 20, 22) and cross-beams (82) and disposed further from the frame (12) than the cross-beams (82) in the unfolded position of the apparatus (10).

13. The apparatus of claim 12, further comprising leg section gussets (94) disposed at corner intersections of the cross-beams (82) and the legs (16, 18, 20, 22) on a same side of the cross-beams (82) as the leg section braces (92).

14. A method of reducing the core temperature of a plurality of human beings simultaneously, comprising:

providing the apparatus (10) of claim 1 with the four legs (16, 18, 20, 22) in the unfolded position of the apparatus;

placing cooling water in the trough (14); and immersing hands and forearms of the plurality of human beings simultaneously in the trough (14).

15. The method of claim 14, wherein placing cooling water in the trough includes placing cooling water in the trough to a depth of three to six inches.

16. The method of claim 14, wherein placing cooling water in the trough includes placing 30 to 44 gallons of cooling water in the trough.

17. The method of claim 16, wherein placing cooling water includes placing cooling water with a temperature less than 80 degrees F.

* * * * *